(12) United States Patent
Kyal et al.

(10) Patent No.: US 9,336,594 B2
(45) Date of Patent: May 10, 2016

(54) CARDIAC PULSE RATE ESTIMATION FROM SOURCE VIDEO DATA

(71) Applicant: Xerox Corporation, Norwalk, CT (US)

(72) Inventors: Survi Kyal, Rochester, NY (US); Lalit Keshav Mestha, Fairport, NY (US)

(73) Assignee: Xerox Corporation, Norwalk, CT (US)

( * ) Notice: Subject to any disclaimer, the term of this patent is extended or adjusted under 35 U.S.C. 154(b) by 277 days.

(21) Appl. No.: 14/200,759

(22) Filed: Mar. 7, 2014

(65) Prior Publication Data

US 2015/0250391 A1    Sep. 10, 2015

(51) Int. Cl.
  G06K 9/00    (2006.01)
  G06T 7/00    (2006.01)
  A61B 5/00    (2006.01)
  A61B 5/024   (2006.01)

(52) U.S. Cl.
  CPC .............. *G06T 7/0014* (2013.01); *A61B 5/0077* (2013.01); *A61B 5/02416* (2013.01); *A61B 5/746* (2013.01); *A61B 2576/00* (2013.01); *G06T 2207/10016* (2013.01); *G06T 2207/30004* (2013.01)

(58) Field of Classification Search
  None
  See application file for complete search history.

(56) References Cited

U.S. PATENT DOCUMENTS

| 4,955,387 | A  | * | 9/1990  | Simonutti  | A61B 5/024 340/574 |
| 8,520,074 | B2 |   | 8/2013  | Wang et al. | |
| 8,587,657 | B2 |   | 11/2013 | Wang et al. | |
| 8,617,081 | B2 |   | 12/2013 | Mestha et al. | |
| 2013/0006123 | A1 | * | 1/2013 | Aoshima | A61B 5/02438 600/483 |
| 2013/0077823 | A1 |   | 3/2013  | Mestha et al. | |
| 2013/0096439 | A1 |   | 4/2013  | Lee et al. | |
| 2013/0147959 | A1 |   | 6/2013  | Wang et al. | |
| 2013/0215244 | A1 |   | 8/2013  | Mestha et al. | |
| 2013/0218028 | A1 |   | 8/2013  | Mestha | |
| 2013/0342670 | A1 |   | 12/2013 | Kyal et al. | |
| 2013/0343614 | A1 |   | 12/2013 | Kyal et al. | |

(Continued)

OTHER PUBLICATIONS

Sun, Yu, Sijung Hu, Vicente Azorin-Peris, Stephen Greenwald, Jonathon Chambers, and Yisheng Zhu. "Motion-compensated noncontact imaging photoplethysmography to monitor cardiorespiratory status during exercise." Journal of biomedical optics 16, No. 7 (2011): 077010-077010.*

(Continued)

*Primary Examiner* — Sumati Lefkowitz
*Assistant Examiner* — Carol Wang
(74) *Attorney, Agent, or Firm* — Philip E. Blair; Fleit Gibbons Gutman Bongini & Bianco P.L.

(57) ABSTRACT

What is disclosed is a system and method for estimating cardiac pulse rate from a video of a subject being monitored for cardiac function. In one embodiment, batches of overlapping image frames are continuously received and processed by isolating regions of exposed skin. Pixels of the isolated regions are processed to obtain a time-series signal per region and a physiological signal is extracted from each region's time-series signals. The physiological signal is processed to obtain a cardiac pulse rate for each region. The cardiac pulse rate for each region is compared to a last good cardiac pulse rate from a previous batch to obtain a difference. If the difference exceeds a threshold, the cardiac pulse rate is discarded. Otherwise, it is retained. Once all the regions have been processed, the retained cardiac pulse rate with a minimum difference becomes the good cardiac pulse rate for comparison on a next iteration.

27 Claims, 8 Drawing Sheets

(56) References Cited

U.S. PATENT DOCUMENTS

| | | |
|---|---|---|
| 2013/0345568 A1 | 12/2013 | Mestha et al. |
| 2013/0345569 A1 | 12/2013 | Mestha et al. |
| 2014/0275832 A1* | 9/2014 | Muehlsteff .......... A61B 5/0205 600/301 |
| 2015/0105670 A1* | 4/2015 | Bresch ................. A61B 5/0077 600/479 |

OTHER PUBLICATIONS

Poh, Ming-Zher, Daniel J. McDuff, and Rosalind W. Picard. "Non-contact, automated cardiac pulse measurements using video imaging and blind source separation." Optics express 18, No. 10 (2010): 10762-10774.*

Kyal et al., "Continuous Cardiac Signal Generation From a Video of a Subject Being Monitored for Cardiac Function", U.S. Appl. No. 13/871,766, filed Apr. 26, 2013.

Mestha et al., "Method and Apparatus for Monitoring a Subject for Atrial Fibrillation", U.S. Appl. No. 13/937,740, filed Jul. 9, 2013.

Mestha et al., "System and Method for Determining Video-Based Pulse Transit Time With Time-Series Signals", U. S. Appl. No. 14/026,739, filed Sep. 13, 2013.

Tanaka et al., "Processing Source Video for Real-Time Enhancement of a Signal of Interest", U.S. Appl. No. 13/745,283, filed Jan. 18, 2013.

* cited by examiner

CARDIAC PULSE RATE ESTIMATION FROM SOURCE VIDEO DATA

TECHNICAL FIELD

The present invention is directed to systems and methods for estimating cardiac pulse rate from a video of a subject being monitored for cardiac function.

BACKGROUND

Assessment of cardio function is vitally important in monitoring neonatal patients, burn or trauma patients, as well as sleep studies and other cases where a continuous measurement of the subject's cardiac pulse rate is required or otherwise desired. Cardiac pulse rate is often measured using an electrocardiogram (ECG) device which often requires adhesive patches, clips, straps, and the like, which may be uncomfortable to wear. The ability to monitor cardiac function by non-contact means is highly desirable in the healthcare industry. Measurements can be made at subject's comfort and will be suitable for long observation/monitoring periods and can provide a record of visual imagery of subjects. Although non-contact methods may not be able to provide details concerning cardiac electrical conduction that ECG offers, video-based methods offer abilities to detect pulsation for long term cardiac function monitoring in a non-contact, unobtrusive manner.

Accordingly, what is needed in this art is a system and method for estimating cardiac pulse rate from a video of a subject being monitored for cardiac function.

INCORPORATED REFERENCES

The following U.S. patents, U.S. patent applications, and Publications are incorporated herein in their entirety by reference.

"Systems And Methods For Non-Contact Heart Rate Sensing", U.S. patent application Ser. No. 13/247,575, by Mestha et al.

"Estimating Cardiac Pulse Recovery From Multi-Channel Source Data Via Constrained Source Separation", U.S. Pat. No. 8,617,081, by Mestha et al.

"Deriving Arterial Pulse Transit Time From A Source Video Image", U.S. patent application Ser. No. 13/401,286, by Mestha.

"Continuous Cardiac Pulse Rate Estimation From Multi-Channel Source Video Data", U.S. patent application Ser. No. 13/528,307, by Kyal et al.

"Video-Based Estimation Of Heart Rate Variability", U.S. patent application Ser. No. 13/532,057, by Mestha et al.

"Determining Cardiac Arrhythmia From A Video Of A Subject Being Monitored For Cardiac Function", U.S. patent application Ser. No. 13/532,128, by Mestha et al.

"Continuous Cardiac Pulse Rate Estimation From Multi-Channel Source Video Data With Mid-Point Stitching", U.S. patent application Ser. No. 13/871,728, by Kyal et al.

"Continuous Cardiac Signal Generation From A Video Of A Subject Being Monitored For Cardiac Function", U.S. patent application Ser. No. 13/871,766, by Kyal et al.

"Determining Cardiac Arrhythmia From A Video Of A Subject Being Monitored For Cardiac Function", U.S. patent application Ser. No. 13/532,128, by Mestha et al.

"Method And Apparatus For Monitoring A Subject For Atrial Fibrillation", U.S. patent application Ser. No. 13/937,740, by Mestha et al.

"System And Method For Determining Video-Based Pulse Transit Time With Time-Series Signals", U.S. patent application Ser. No. 14/026,739, by Mestha et al.

BRIEF SUMMARY

What is disclosed is a system and method for estimating cardiac pulse rate from a video of a subject being monitored for cardiac function. One embodiment of the present method involves performing the following. First, batches of time-sequential image frames of video of a subject being monitored for cardiac function are continuously received. The batches of image frames are captured by a video imaging device in real-time for continuous processing. Temporally successive batches may partially overlap. Batches of image frames are processed as follows. A) For the current batch, at least two regions of exposed skin of the subject are isolated in the image frames comprising that batch. The isolated regions are areas of the subject's body where a physiological (photoplethysmographic) signal corresponding to the subject's cardiac function was registered by one or more imaging channels of the video imaging device being used to capture that video. Regions of exposed skin may partially overlap. B) For each of the isolated regions in the image frames of the current batch, the following are performed: (i) pixels of the isolated region are processed to obtain a time-series signal for this region; (ii) a physiological signal corresponding to the subject's cardiac function is extracted from the time-series signal; (iii) the physiological signal is processed to obtain a cardiac pulse rate associated with this region; (iv) the cardiac pulse rate is compared to a last good cardiac pulse rate for the subject determined by having processed a previous batch. This comparison generates a difference (delta) between last good cardiac pulse rate and different region's cardiac pulse for the current batch. On a first iteration, the comparison is performed using an initial or default cardiac pulse rate; and (iv) in response to the delta exceeding a pre-defined threshold level, this region's cardiac pulse rate is discarded. Otherwise, this region's cardiac pulse rate is retained. Once all regions for the current batch have been processed accordingly, the retained cardiac pulse rate with a minimum delta is determined to be the next good cardiac pulse rate for the current batch. If there are more than one region with small delta values within a cluster one could take an average of all selected region's cardiac pulse rate to determine to be the next good cardiac pulse. This next good cardiac pulse rate is used for comparison purposes on a next iteration. Various embodiments are disclosed.

Features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

What is disclosed is a system and method for estimating cardiac pulse rate from a video of a subject being monitored for cardiac function.

Non-Limiting Definitions

"Photoplethysmography" refers to the study of signals containing relative blood volume changes in the blood vessels close to the skin surface. A photoplethysmographic (PPG) signal contains important information about the subject's cardiac function.

"Cardiac function" refers to the function of the heart and, to a larger extent, to the entire cardio-vascular system. In most species, a heart muscle repeatedly contracts to push a volume of blood into the body's vascular network. Cardiac function can be impacted by factors including: age, stress, disease, cardiac health, and the like. Cardiac function can be affected by environmental conditions such as: altitude and pressure.

"Cardiac pulse rate" or "cardiac pulse frequency" refers to the rate of heart beats per minute (bpm). In humans, the cardiac pulse frequency range is about 50 bpm to about 240 bpm. Each species has their own normal cardiac pulse frequency. For an adult athlete, the resting heart rate will be 40 to 60 bpm. The frequency range of the cardiac pulse for animals also varies in a similar manner. For example, a cat has a cardiac pulse of 120 to 140 bpm, a mouse has a cardiac pulse of 450-750 bpm and an elephant has a cardiac pulse of 25-35 bpm. Each species has its own cardiac pulse frequency range and thus its own "normal" heart rate. A normal resting heart rate for a healthy adult can range from 60 to 100 bpm but may drop to as low as 40 bpm during sleep and may go as high as 240 bpm during vigorous exercise.

A "subject" refers to a living person with a cardiac function. Although the terms "person" or "patient" may be used throughout this disclosure, it should be appreciated that the subject may not be human. As such, use of the terms "human", "person" or "patient" is not to be viewed as limiting the scope of the appended claims strictly to human beings.

A "video", as is generally understood, is a time-varying sequence of image frames captured using a video imaging device. The video may contain other components such as, audio, time reference signals, frame rate, and the like.

Figure 1:
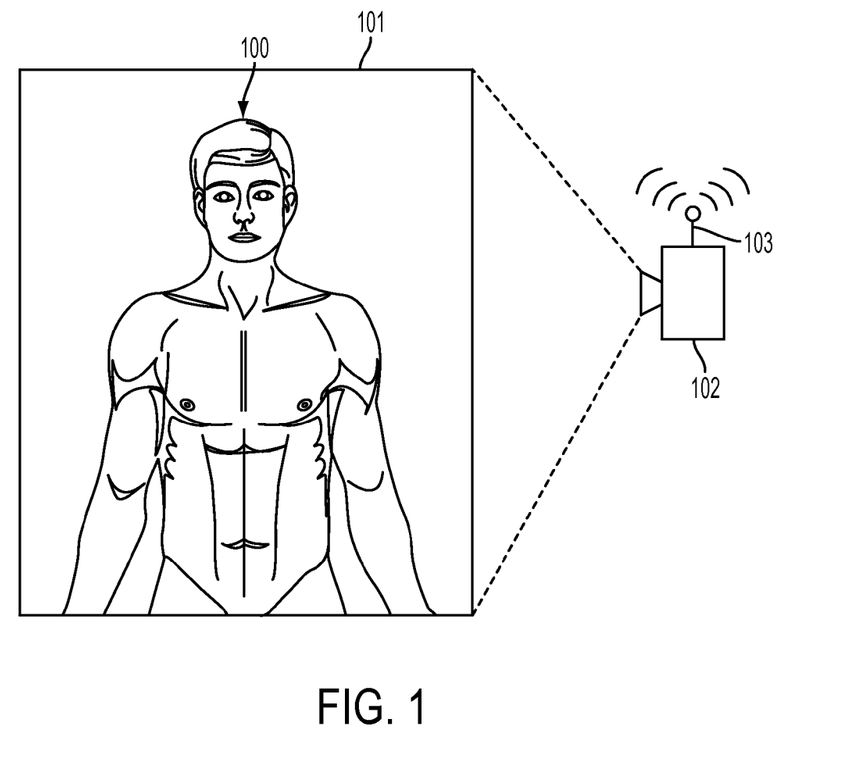
FIG. 1 shows a video image device capturing real-time video of a subject.

A "video imaging device" refers to a single-channel or multi-channel video camera for acquiring a video. The video imaging device is capable of registering a photoplethysmographic signal on at least one imaging channel. FIG. 1 shows a video imaging device 102 actively capturing video 101 of a subject 100. The video is communicated to a remote device via a wireless element 103, shown as an antenna. Video imaging devices include: a color video camera, a monochrome video camera, an infrared video camera, a multispectral video camera, a hyperspectral video camera, and a hybrid camera comprising any combination hereof. The video imaging device may have a plurality of outputs from which the video can be retrieved or otherwise received on a per-channel basis and may incorporate memory and a storage device. Multi-channel video imaging systems comprising standard video cameras and those with spectral sensors are available from different vendors in various streams of commerce. Video imaging devices may incorporate one or more processors executing machine readable program instructions for analyzing batches of image frames in real-time, in accordance with the teachings hereof.

"Receiving image frames" is intended to be widely construed and includes: retrieving, capturing, acquiring, or otherwise obtaining image frames for processing. The image frames can be retrieved from a memory or storage device of the video imaging device or retrieved from a media such as a CDROM or DVD. Video image frames can be obtained from a remote device over a network or downloaded from a web-based system or application which makes image frames available for processing. Video image frames can also be retrieved using an application such as those which are widely available for handheld wireless cellular devices and processed on the user's smartphone or other handheld computing device such as an iPad or tablet device.

Figure 2:
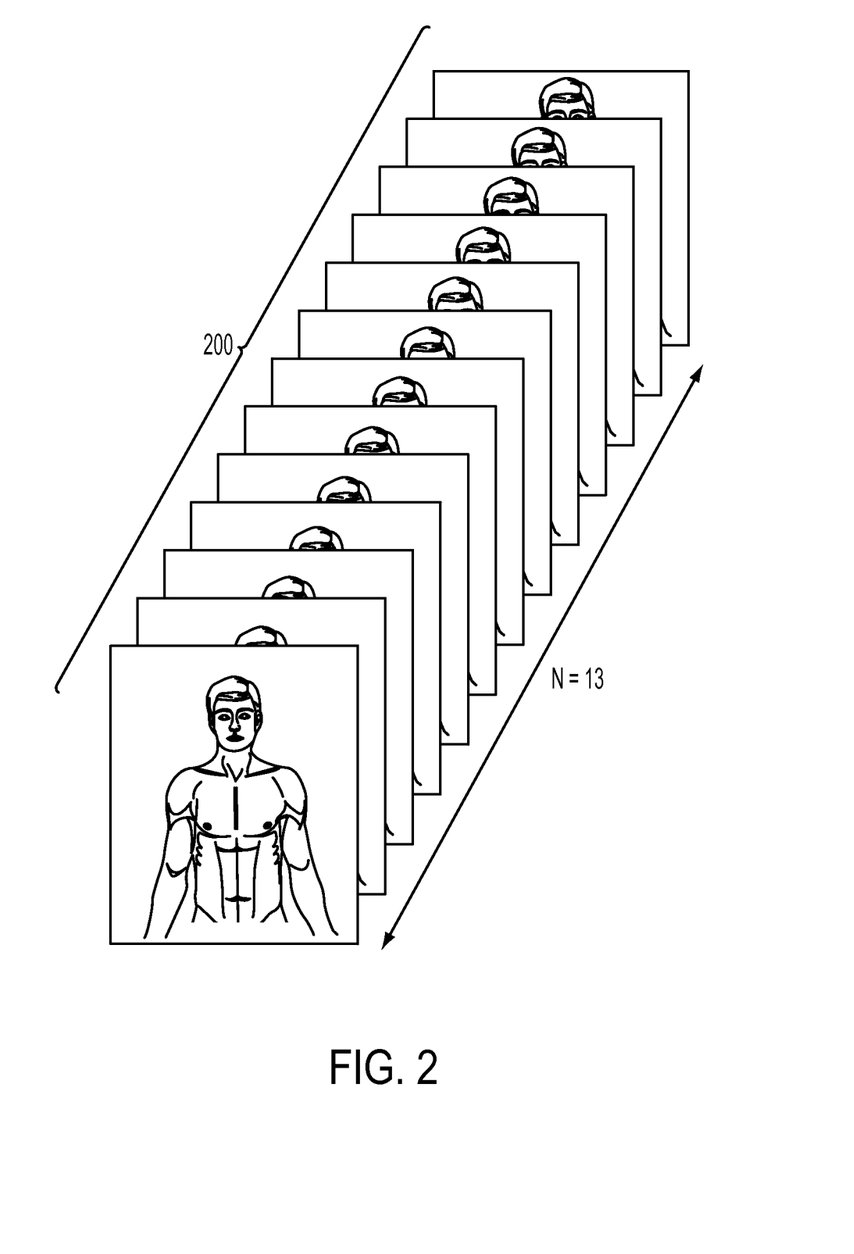
FIG. 2 shows a batch of image frames of the video acquired by the video imaging device of FIG. 1.

A "batch of image frames" refers to a plurality of time-sequential image frames of a video of the subject. FIG. 2 shows an example batch of 13 image frames (collectively at 200) of the subject acquired by the video imaging device of FIG. 1. Batches of image frames do not have to be the same size and may vary dynamically during processing. A size of a given batch of video image frames should at least be of a duration which captures one cardiac cycle of the subject. Batches of image frames can be defined for processing utilizing a sliding window. In one example, the sliding window defines each successive batch with 1 second of new image frames and 29 seconds of image frames from the previous batch, (i.e., a 96% overlap). A size of a batch can be pre-defined as needed. Batches of image frames are processed to isolate regions of exposed skin.

Figure 3:
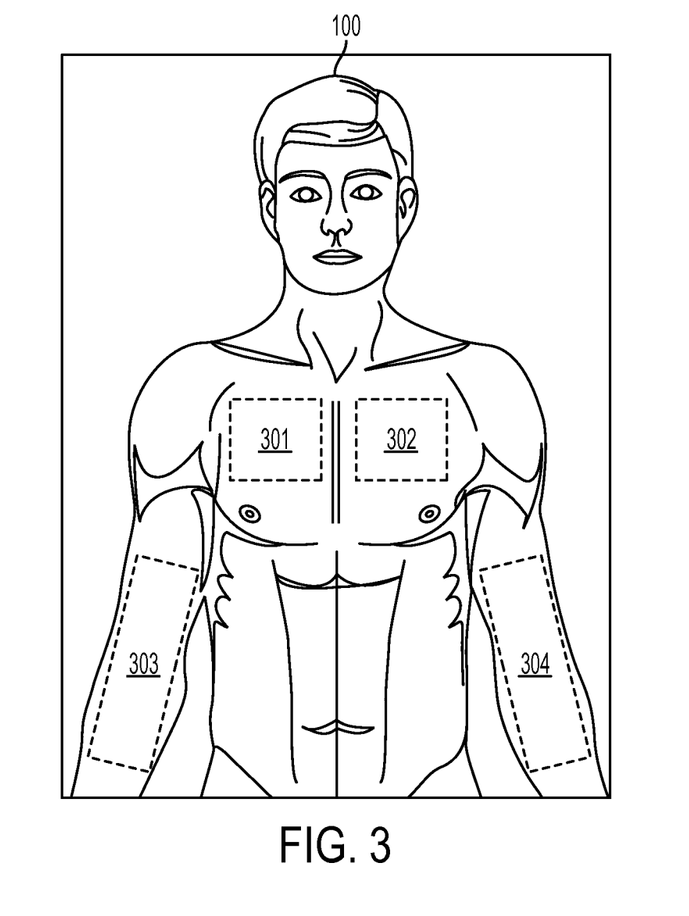
FIG. 3 shows one of the image frames of the batch of FIG. 2 with various regions of exposed skin having been identified for processing.

A "region of exposed skin" refers to an unobstructed view of the subject's skin as seen through the lens of the video imaging device. Regions of exposed skin are isolated in the image frames of the batch where a physiological signal corresponding to the subject's cardiac function was registered by one or more imaging channels of the video imaging device used to capture that video. FIG. 3 shows one of the image frames of the batch of FIG. 2 with a rubber-band box having been drawn around various isolated regions of exposed skin (at 301, 302, 303 and 304). It should be appreciated that the isolated regions of FIG. 3 are illustrative for explanatory purposes. Other regions may be identified. As such, FIG. 3 should not be viewed as limiting the scope of the appended claims solely to the identified regions of exposed skin shown. A region of exposed skin has a minimum size. Regions do not have to be the same size. The size of a given region of exposed skin will vary depending on the application and thus a discussion as to a specific size of a region is omitted. Since a premature baby in a neonatal intensive care unit (NICU) has less skin surface than an adult, the video camera should preferably be zoomed-in on the baby to capture larger regions of exposed skin and thus obtain larger numbers of pixels of skin surface for processing.

Figure 5:
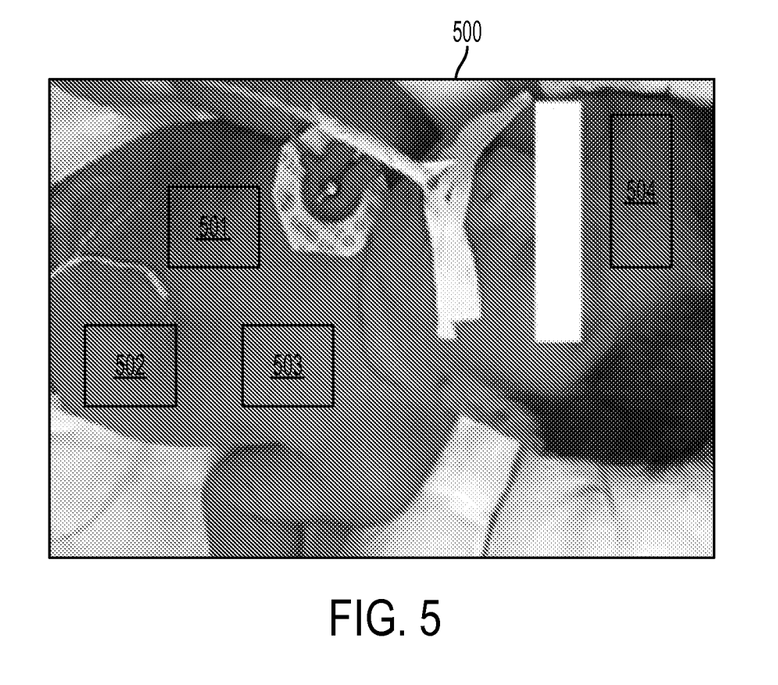
FIG. 5 shows one image of the infant of FIG. 4 with four regions of exposed skin have been identified for processing.

"Isolating a region of exposed skin" in the image frames of a given batch can be effectuated using image processing techniques which include, for instance object identification, pattern recognition, face detection and facial recognition methods. Regions can be identified in image frames using a pixel classification method. Methods for classifying pixels in an image are disclosed in: "Determining A Total Number Of People In An IR Image Obtained Via An IR Imaging System", U.S. Pat. No. 8,520,074, by Wang et al., which discloses a ratio method for classifying pixels in an image; "Determining A Number Of Objects In An IR Image", U.S. Pat. No. 8,587,657, by Wang et al., which discloses a correlation method and a best fitting reflectance method for classifying pixels in an image; and "Determining A Pixel Classification Threshold For Vehicle Occupancy Detection", U.S. patent application Ser. No. 13/324,308, by Wang et al., which discloses a method for determining a threshold used for pixel classification. Other methods include color and texture identification, analysis of spatial features, spectral information, and a user input. A user or technician may use a mouse or a touchscreen display to identify regions of exposed skin in the image frames of the video (as shown in FIG. 5). Pixels in each isolated region are processed to obtain a time-series signal for each region.

A "time-series signal" is a signal which contains frequency components related to the subject's cardiac pulse frequency. A time series signal is generated by processing pixels in each of the isolated regions of batches of video image frames. One method for obtaining a time-series signal for a given region of isolated pixels involves averaging pixel values within the isolated regions across all the image frames in the batch. An average is then computed of all pixel values to obtain a channel average per frame. A global channel average can be computed, for each channel, by adding the channel averages across multiple frames and dividing by the total number of frames. The channel average is subtracted from the global channel average and the result is divided by a global channel standard deviation to obtain a zero-mean unit variance time-series signal for each isolated region in each batch of image frames. The time-series signal contains frequency components. The time-series signals may be normalized and are then subjected to a pre-filtering to remove undesirable frequencies. Segments of the time-series signal can be weighted, as desired. Such a weighting may be applied over one or more segments while other signal segments are not weighted. Methods for weighting signal segments are widely understood in the signal processing arts. It should be appreciated that the time-series signal may be received or retrieved from a remote device such as a computer workstation over a wired or wireless network with the captured video having been communicated directly to the remote device for generation of the time-series signal on a continuous basis. The time-series signals are generated in real-time from a streaming video for continuous cardiac function monitoring and assessment. A time-series signal can be identified using a measure of closeness determined with respect to a reference signal such as an ECG signal obtained using non-invasive electro-optic techniques. The reference signal facilitates the identification of a time-series signal in the source video utilizing a measure of closeness. Methods for processing video image frames to identify a time-series signal and for enhancing that signal are disclosed in: "Processing Source Video For Real-Time Enhancement Of A Signal Of Interest", U.S. patent application Ser. No. 13/745,283, by Tanaka et al. The video image frames may be processed to remove undesirable periodic signals and background noise as disclosed in: "Removing Environment Factors From Signals Generated From Video Images Captured For Biomedical Measurements", U.S. patent application Ser. No. 13/401,207, by Mestha et al. The time-series signal obtained for each region is processed to obtain a physiological signal. The physiological signal is, in turn, processed to extract a cardiac pulse rate. The obtained cardiac pulse rate is then compared, on a per-region basis, to a last good cardiac pulse rate obtained for the subject by having processed a previous batch of image frames. As batches of image frames are processed in real-time, a "good" cardiac pulse rate is determined for each batch.

A "good cardiac pulse rate" means a retained cardiac pulse rate from a current batch which has a minimum difference (i.e., a smallest delta) between several regions selected to monitor cardiac pulse when compared to the last good cardiac pulse rate obtained from a previous batch of image frames. Note that, if all of the cardiac pulse rates for each region of a given batch of image frames are discarded, (i.e., none are retained) due to, for instance, excessive movement having occurred during video acquisition of those image frames or none of the determined deltas is less than the threshold level, then there would be no "good" cardiac pulse rate for the current batch. In this instance, on a next iteration of processing a next batch of image frames, retained cardiac pulse rates would be compared to the last known "good" cardiac pulse rate. In various embodiments hereof, if none of the cardiac pulse rates are retained for a given batch, an alert signal is initiated which provides an indication that all the cardiac pulse rates for the current batch were discarded.

Example Image Capturing System

Figure 4:
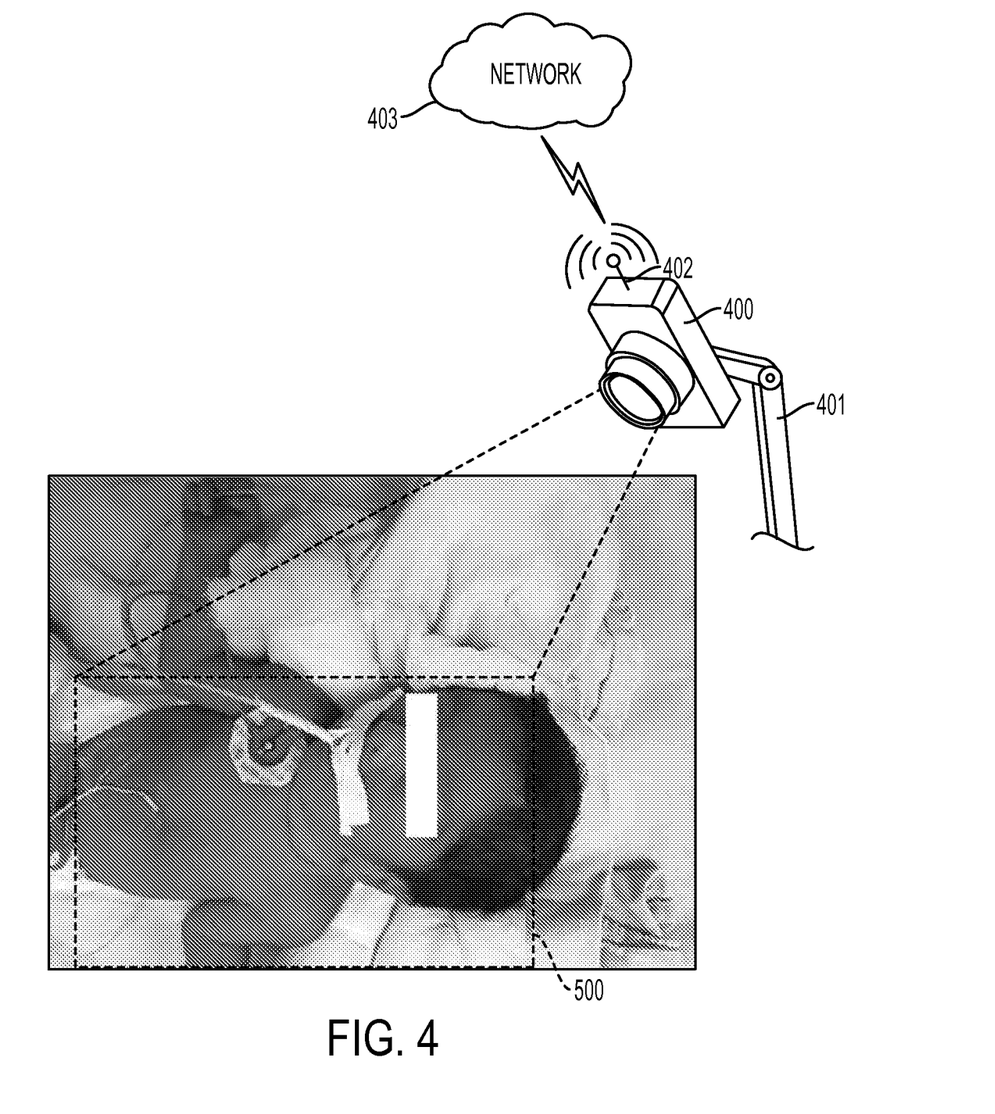
FIG. 4 illustrates an example video image camera capturing a multi-channel video signal of an infant in a neonatal intensive care unit.

Reference is now being made to FIG. 4 which illustrates an example video image camera 400 capturing a multi-channel signal of a baby in a neonatal intensive care unit (NICU) shown resting her head on a cloth while parts of her body are partially covered.

In FIG. 4, the video camera is rotatably fixed to a mounting arm 401 such that the video camera's field of view can be directed by a nurse (not shown) onto an area of exposed skin of the premature infant for continuous monitoring of cardiac function. Support arm 401 is preferably mounted on wheels so that the video system can be moved from bed to bed and room to room throughout the facility. Although the premature infant patient is shown in a supine position, it should be appreciated that video images of a subject can be captured while the subject is seated in wheelchair, standing, walking or running on a treadmill, or pedaling a cycle. The embodiment of FIG. 4 is not to be viewed as limiting the scope of the appended claims in any respect.

Video imaging device 400 is zooming-in on the premature infant such that images are captured thereof will have larger regions of exposed skin and thus contain more pixels. The captured video image frames of FIG. 4 comprise multi-channel source data. FIG. 5 shows one image frame from the batch of image frame of FIG. 4.

Video camera 400 has imaging sensors which may be a single sensor or a sensor array including a plurality of individual or separate sensor units. The imaging sensors may take a variety of forms each having the capability of detecting changes in the status of sensors and outputting an alarm, notice, report, and the like if a change in any hardware or software of the camera has been detected. A central processor, internal to the video imaging device, is in communication with an internal memory. Antenna 402 communicates the video image frames to one or more remote devices via network 403 by a wired or wireless connection. A remote device may be a workstation with a graphical display device, or a handheld device such as an iPhone, iPad, or notebook. Techniques for placing devices in networked communication are well established. Therefore, a further discussion as to specific techniques for networking is omitted for brevity. Video imaging device 400 may be connected via other means such as cable, or any other communication means.

In accordance with the methods disclosed herein, image frames are processed to isolate regions of exposed skin of the subject in the video being monitored for cardiac function. FIG. 5 is a close-up image of the baby of FIG. 4 wherein four regions of exposed skin (501, 502, 503, 504) have been isolated.

Flow Diagram of One Example Embodiment

Figure 6:
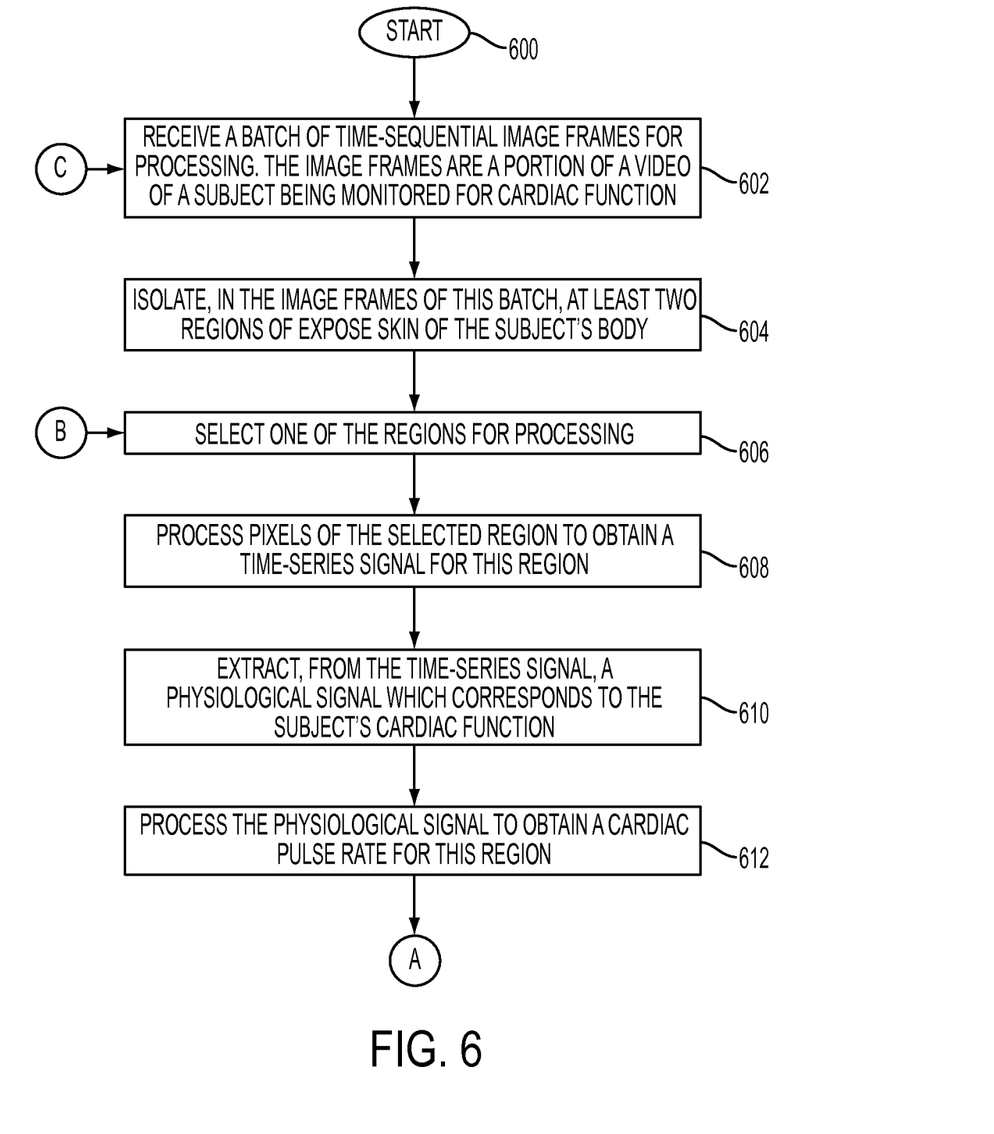
FIG. 6 is a flow diagram which illustrates one example embodiment of the present method for continuous estimation of cardiac pulse rate from video of a subject being monitored for cardiac function in a non-contact, remote sensing environment.

Reference is now being made to the flow diagram of FIG. 6 which illustrates one embodiment of the present method for continuous estimation of cardiac pulse rate from a video of a subject being monitored for cardiac function in a non-contact, remote sensing environment. Flow processing begins at step 600 and immediately proceeds to step 602.

At step 602, receive a batch of time-sequential image frames for processing. The batch of image frames are a portion of the video acquired in a continuous manner with a video imaging device. One example video imaging device is shown and discussed with respect to FIGS. 1 and 4.

At step 604, isolate, in the image frames of this batch, at least two regions of exposed skin of the subject's body. FIG. 3 shows various isolated regions of exposed skin. FIG. 5 shows various isolated regions of exposed skin on the premature baby.

At step 606, select a first region for processing. The selection can be performed manually by a technician viewing the batch of image frames as they are being received for processing or by an algorithm which identifies regions of exposed skin in the image frames using image processing techniques.

At step 608, process pixels of this region to obtain a time-series signal.

At step 610, extract, from the time-series signal, a physiological signal which corresponds to the subject's cardiac function.

At step 612, process the physiological signal to obtain a cardiac pulse rate.

Figure 7:
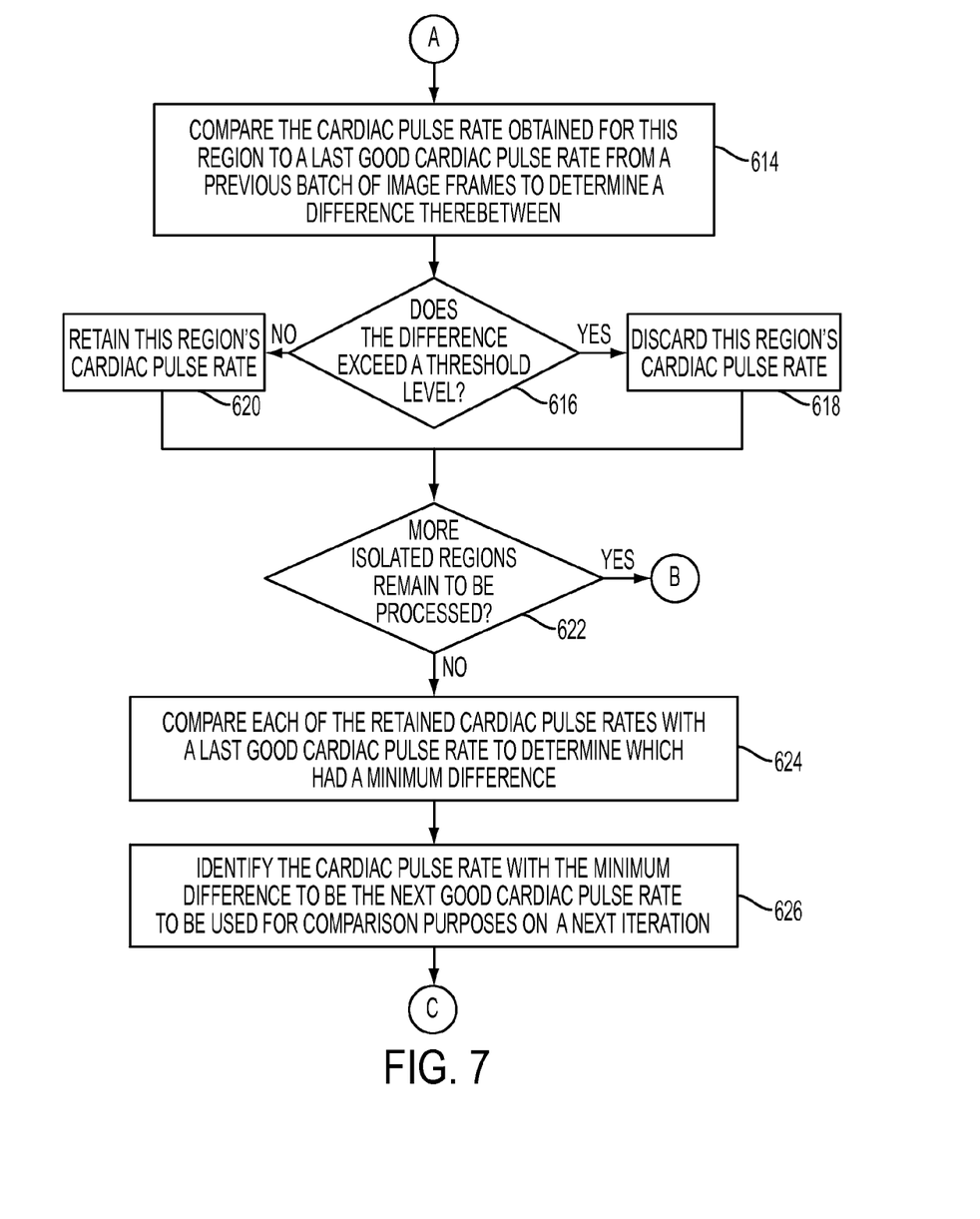
FIG. 7 is a continuation of the flow diagram of FIG. 6 with flow processing continuing with respect to node A.

Reference is now being made to the flow diagram of FIG. 7 which is a continuation of the flow diagram of FIG. 6 with flow processing continuing with respect to node A;

At step 614, compare the cardiac pulse rate for this region to a last good cardiac pulse rate for the subject from a previous batch of image frames to determine a difference (or delta) therebetween. On a first iteration, this comparison is performed using an initial cardiac pulse rate pre-set for the subject.

At step 616, a determination is made whether the difference exceeds a threshold. If so, then, at step 618, discard this region's cardiac pulse rate. Otherwise, at step 620, retain this region's cardiac pulse rate.

At step 622, a determination is made whether more isolated regions remain to be processed. If so, then processing repeats with respect to node B wherein, at step 606, a next isolated region is selected or otherwise identified for processing. Processing repeats in a similar manner for each region isolated in the image frames of the current batch.

At step 624, compare each of the retained cardiac pulse rates with a last good cardiac pulse rate to determine which had a minimum difference.

At step 626, identify the cardiac pulse rate with the minimum difference (smallest delta) within a pre-defined range to be the next good cardiac pulse rate for the current batch. The next good cardiac pulse rate will then be used for comparison purposes on a next iteration. Thereafter, in this embodiment of continuous processing, flow continues with respect to node C wherein, at step 602, a next batch of image frames is processed. In this embodiment, processing repeats in a continuous manner until the system is turned OFF or video acquisition otherwise ceases. In other embodiments, video of a desired duration such as, for example, 30 minutes is acquired and processed in real-time. A timer can be pre-set to a desired length of time with video acquisition and further processing terminating upon expiration of the limit set by the timer.

In another embodiment, the cardiac pulse rate is continuously analyzed to determine whether an alert condition exists. Such a determination can be made using, for example, one or more threshold levels which may be retrieved from a memory, storage device, or data base, or which may be set or pre-set by a technician or medical professional. The alert condition can be determined by a visual examination of the cardiac pulse rate, or by an algorithm monitoring these signals or by analyzing any of the intermediate results obtained from processing the image frames of a given batch. If it is determined that an alert condition exists then an alert signal is initiated. The alert signal can be sent to a technician, nurse, medical practitioner, and the like. Such an alert signal may take the form of a tone or bell, or a visual or audible message being activated at a nurse's station. The alert may be a message such as a text, audio, and/or video. The alert may take the form of a blinking light on a control panel or display device associated with the present system.

It should also be appreciated that the flow diagrams depicted herein are illustrative. One or more of the operations may be performed in a differing order. Other operations may be added, modified, enhanced, or consolidated. Variations thereof are intended to fall within the scope of the appended claims.

Example Networked System

Figure 8:
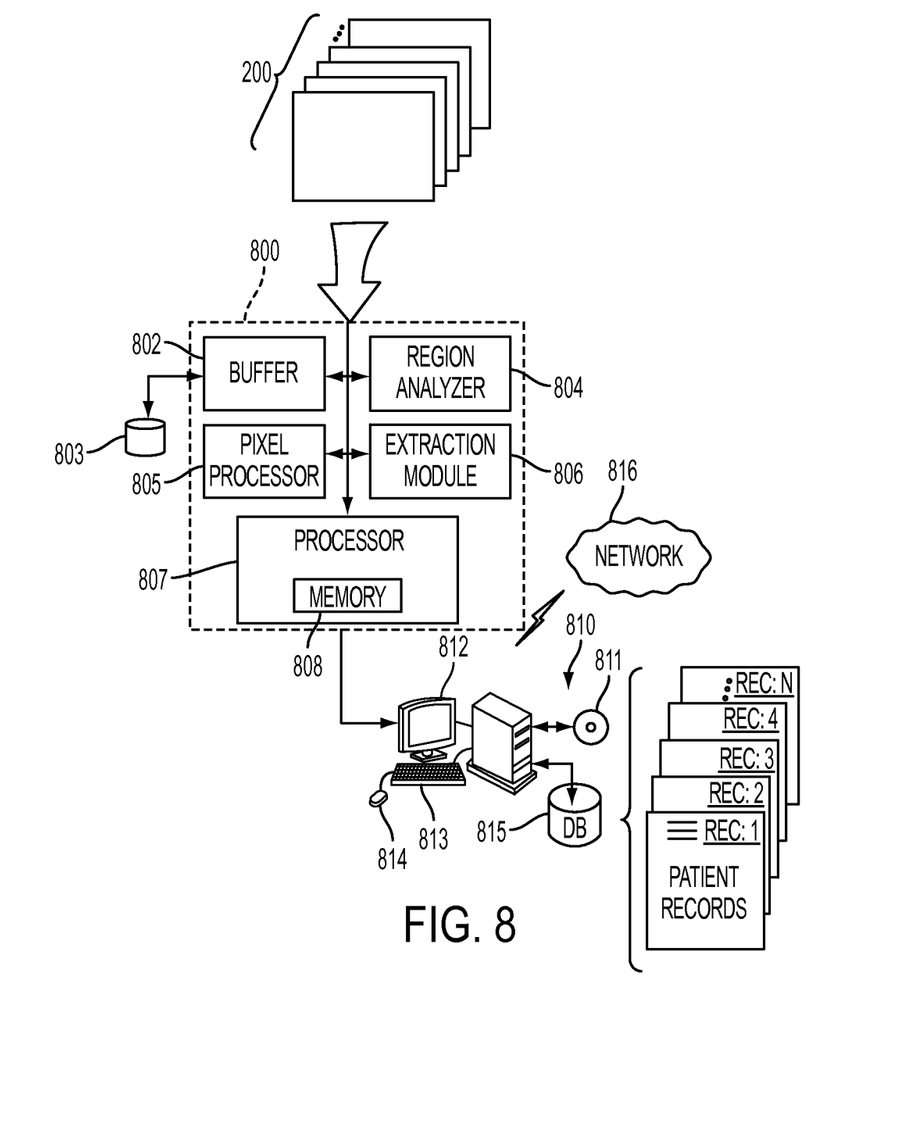
FIG. 8 is a block diagram of an example batch processing system for performing various aspects of the teachings hereof as described with respect to the flow diagram of FIGS. 6-7.

Reference is now being made to FIG. 8 which illustrates a block diagram of one example batch processing system 800 for performing various aspects of the teachings hereof as discussed with respect to the flow diagrams of FIGS. 6 and 7.

In FIG. 8, batch processing system 800 receives at least a batch of image frames into Buffer 802 which may be further configured to also store data, mathematical formulas and other representations to facilitate processing of the image in accordance with the teachings hereof. Such data can be stored to storage media 803. Region Analyzer 804 processes the image frames of the batch to identify a plurality of skin surface regions. Pixel Processor Module 805 processes the pixels in each of the identified regions to obtain a time-series signal for each region. Extraction Module 806 receives the time-series signals and extracts a physiological signal therefrom which corresponds to the subject's cardiac function. Processor 807 and memory 808 process the physiological signals to obtain, for each region, a cardiac pulse rate. Processor 807 further executes machine readable program instructions which determine which of the cardiac pulse rates should be retained or discarded based on a result of the differences determined as a result of having compared each of the cardiac pulse rates to the last good cardiac pulse rate. In other embodiments, processor 807 further determines whether any movement occurred which is likely to have skewed any of the obtained cardiac pulse rates. Further, the processor and memory support the processing requirements of the modules and processing units of the batch processing system 800. System 800 is shown in communication with a workstation.

Workstation 810 has a computer case 12 which houses a motherboard with a processor and memory, a communications link such as a network card, graphics card, and the like. The workstation has hardware which reads/writes to a computer readable media 811 such as a floppy disk, CD-ROM, DVD, USB-Drive, etc. The workstation further includes a display device 812 such as a CRT, LCD, touch screen, etc., a keyboard 813 and a mouse 814. The workstation is shown implementing a database 816 wherein patient records are stored, manipulated, and retrieved in response to a query. Such records, in various embodiments, take the form of patient medical history stored in association with information identifying the patient along with information regarding the regions processed, camera settings, mathematical representations and data values used to process the batch of image frames, medical diagnosis, and the like. Although the database is shown as an external device, the database may be internal to the workstation mounted, for example, on a hard disk therein. The workstation is placed in communication with one or more remote devices over a network 816, which may comprise a wired or wireless connection. Any of the values, images, results, and the like, which are obtained or produced by the system of FIG. 8 may be communicated to one or more remote devices over the network. It should be appreciated that the workstation has an operating system and other specialized software configured to display a wide variety of numeric values, text, scroll bars, pull-down menus with user selectable options, and the like, for entering, selecting, or modifying information displayed on the display device. The embodiment shown is illustrative. Although shown as a desktop computer, it should be appreciated that the workstation can be a smartphone, laptop, mainframe, client/server, or a special purpose computer such as an ASIC, circuit board, dedicated processor, or the like.

Each module of the batch processing system of FIG. 8 may have a specialized processor executing machine readable program instructions for performing their intended functions. A module may comprise an ASIC, an electronic circuit, a special purpose processor, and the like. A plurality of modules may be executed by a single special purpose computer system or a plurality of computer systems operating in parallel. Modules may include software/hardware which may further comprise an operating system, drivers, controllers, and other apparatuses some or all of which may be connected via a network. Various modules may designate one or more components. A plurality of modules may collectively perform a single function.

Various aspects of the systems and methods described herein are intended to be incorporated in an article of manufacture which may be shipped, sold, leased, or otherwise provided separately either alone or as part of a product suite. The above-disclosed features and functions or alternatives thereof, may be combined into other systems and applications. Presently unforeseen or unanticipated alternatives, modifications, variations, or improvements may become apparent and/or subsequently made by those skilled in the art and, further, may be desirably combined into other different systems or applications. Changes to the above-described embodiments may be made without departing from the spirit and scope of the invention.

The teachings of any printed publications including patents and patent applications, are each separately hereby incorporated by reference in their entirety.

What is claimed is:

1. A method for continuous estimation of cardiac pulse rate from video of a subject being monitored for cardiac function in a non-contact, remote sensing environment, the method comprising:
    repeatedly receiving batches of time-sequential image frames captured by at least one video imaging device of a subject being monitored for cardiac function; and
    processing successive batches of image frames, comprising:
    A) isolating, in said image frames, at least two regions of exposed skin of said subject where a signal corresponding to said subject's cardiac function was registered by at least one imaging channel of said video imaging device;
    B) for each of said isolated regions, performing:
        (i) processing pixels of said isolated region to obtain a time-series signal for this region;
        (ii) extracting, from said time-series signals, a physiological signal corresponding to said subject's cardiac function;
        (iii) processing said physiological signal to obtain a cardiac pulse rate for this region;
        (iv) comparing said cardiac pulse rate for this region to a last good cardiac pulse rate for said subject determined by having processed a previous batch to obtain a difference therebetween, on a first iteration said comparison being performed using an initial cardiac pulse rate determined for said subject; and
        (v) in response to said difference exceeding a threshold level, discarding this region's cardiac pulse rate, otherwise retaining this region's cardiac pulse rate; and
    C) in response to having performed steps A and B, determining that a retained cardiac pulse rate with a minimum difference between a last good cardiac pulse rate for a previous batch to be a next good cardiac pulse rate for a current batch, said next good cardiac pulse rate being used for comparison purposes on a next iteration.

2. The method of claim 1, wherein said video imaging device is any of: a color video camera, a monochrome video camera, an infrared video camera, a multispectral video imaging device, a hyperspectral video camera, and a hybrid camera comprising any combination hereof.

3. The method of claim 1, wherein pixels associated with said regions of exposed skin are isolated in said image frames using any of: pixel classification, object identification, thoracic region recognition, color, texture, spatial features, spectral information, pattern recognition, face detection, facial recognition, and a user input.

4. The method of claim 1, wherein said regions of exposed skin may or may not partially overlap.

5. The method of claim 1, wherein said batch of image frames partially temporally overlaps with the image frames of a previous batch.

6. The method of claim 1, wherein said threshold used for determining whether a difference between this region's cardiac pulse rate and the last good cardiac pulse rate for said subject is a function of any of: an age of said subject, a health of said subject, and a state of the subject's cardiac function.

7. The method of claim 1, further comprising filtering said time-series signal with a low and high cutoff frequency defined as a function of said subject's cardiac pulse frequency.

8. The method of claim 7, further comprising any of:
    performing a non-parametric spectral density estimation on said filtered signal;
    performing a parametric spectral density estimation on said filtered signal; and performing automatic peak detection on said filtered signal.

9. The method of claim 1, further comprising detrending said time-series signal to remove low frequency and non-stationary components.

10. The method of claim 1, further comprising determining whether a movement occurred during video acquisition of the current batch of image frames which is likely to have skewed said cardiac pulse rate obtained for this region, and in response to said movement exceeding a threshold level of movement, discarding this region's cardiac pulse rate, otherwise retaining this region's cardiac pulse rate.

11. The method of claim 10, wherein determining whether a movement occurred during video acquisition comprises any of:
analyzing pixels of said isolated region to determine whether a movement occurred;
using a motion detector to determine when a movement occurred; and
visually observing said subject.

12. The method of claim 11, wherein analyzing pixels of said isolated region to identify movement comprises any of:
a change in a location of a center pixel within said isolated region;
a change in a size of said isolated region;
a change in a shape of said isolated region;
a change in a color of said isolated region; and
a residual from frame differencing.

13. The method of claim 1, further comprising analyzing said physiological signal to determine an occurrence of any of: Cardiac Arrhythmia, Cardiac Stress, Cardiac Failure, and Heart Disease.

14. The method of claim 1, further comprising communicating said cardiac pulse rate to any of: a memory, a storage device, a display device, and a remote device over a network.

15. A system for continuous estimation of cardiac pulse rate from video of a subject being monitored for cardiac function in a non-contact, remote sensing environment, the system comprising:
a processor in communication with a memory, said processor receiving batches of time-sequential image frames captured by at least one video imaging device of a subject being monitored for cardiac function and executing machine readable instructions for processing successive batches of image frames, comprising:
A) isolating, in said image frames, at least two regions of exposed skin of said subject where a signal corresponding to said subject's cardiac function was registered by at least one imaging channel of said video imaging device;
B) for each of said isolated regions, performing:
(i) processing pixels of said isolated region to obtain a time-series signal for this region;
(ii) extracting, from said time-series signals, a physiological signal corresponding to said subject's cardiac function; (iii) processing said physiological signal to obtain a cardiac pulse rate for this region;
(iv) comparing said cardiac pulse rate for this region to a last good cardiac pulse rate for said subject determined by having processed a previous batch to obtain a difference therebetween, on a first iteration said comparison being performed using an initial cardiac pulse rate determined for said subject; and
(v) in response to said difference exceeding a threshold level, discarding this region's cardiac pulse rate, otherwise retaining this region's cardiac pulse rate;
C) in response to having performed steps A and B, determining that a retained cardiac pulse rate with a minimum difference between a last good cardiac pulse rate for a previous batch to be a next good cardiac pulse rate for a current batch, said next good cardiac pulse rate being used for comparison purposes on a next iteration; and
D) communicating said next good cardiac pulse rate to a display device.

16. The system of claim 15, wherein said video imaging device is any of: a color video camera, a monochrome video camera, an infrared video camera, a multispectral video imaging device, a hyperspectral video camera, and a hybrid camera comprising any combination hereof.

17. The system of claim 15, wherein pixels associated with said regions of exposed skin are isolated in said image frames using any of: pixel classification, object identification, thoracic region recognition, color, texture, spatial features, spectral information, pattern recognition, face detection, facial recognition, and a user input.

18. The system of claim 15, wherein said regions of exposed skin partially overlap.

19. The system of claim 15, wherein said batch of image frames partially temporally overlaps with the image frames of a previous batch.

20. The system of claim 15, wherein said threshold used for determining whether a difference between this region's cardiac pulse rate and the last good cardiac pulse rate for said subject is a function of any of: an age of said subject, a health of said subject, and a state of the subject's cardiac function.

21. The system of claim 15, further comprising filtering said time-series signal with a low and high cutoff frequency defined as a function of said subject's cardiac pulse frequency.

22. The system of claim 21, further comprising any of:
performing a non-parametric spectral density estimation on said filtered signal;
performing a parametric spectral density estimation on said filtered signal; and
performing automatic peak detection on said filtered signal.

23. The system of claim 15, further comprising detrending said time-series signal to remove low frequency and non-stationary components.

24. The system of claim 15, further comprising determining whether a movement occurred during video acquisition of the current batch of image frames which is likely to have skewed said cardiac pulse rate obtained for this region, and in response to said movement exceeding a threshold level of movement, discarding this region's cardiac pulse rate, otherwise retaining this region's cardiac pulse rate.

25. The system of claim 24, wherein determining whether a movement occurred during video acquisition comprises any of:
analyzing pixels of said isolated region to determine whether a movement occurred;
using a motion detector to determine when a movement occurred; and
visually observing said subject.

26. The system of claim 25, wherein analyzing pixels of said isolated region to identify movement comprises any of:
a change in a location of a center pixel within said isolated region;
a change in a size of said isolated region;
a change in a shape of said isolated region;
a change in a color of said isolated region; and
a residual from frame differencing.

27. The system of claim 15, further comprising analyzing said physiological signal to determine an occurrence of any of: Cardiac Arrhythmia, Cardiac Stress, Cardiac Failure, and Heart Disease.

* * * * *